United States Patent
Chen et al.

(10) Patent No.: US 10,434,148 B2
(45) Date of Patent: Oct. 8, 2019

(54) PREPARATION METHOD OF ALBUMIN PEPTIDE COMBINATION HAVING THE ACTION OF INHIBITING THE PROLIFERATION OF CANCER CELLS

(71) Applicants: Dongliang Chen, Hong Kong (CN); Nascent Peptide Biotechnology Limited, Hong Kong (CN)

(72) Inventors: Dongliang Chen, HongKong (CN); Yang Zhang, Wuhan (CN); Cong Zhou, Wuhan (CN)

(73) Assignees: Dongliang Chen (HK); Nascent Peptide Biotechnology Limited (HK)

( * ) Notice: Subject to any disclaimer, the term of this patent is extended or adjusted under 35 U.S.C. 154(b) by 0 days.

(21) Appl. No.: 15/642,289

(22) Filed: Jul. 5, 2017

(65) Prior Publication Data
US 2018/0008678 A1    Jan. 11, 2018

(30) Foreign Application Priority Data
Jul. 6, 2016  (CN) .......................... 2016 1 0527097

(51) Int. Cl.
*A61K 36/8994* (2006.01)
*A61K 38/38* (2006.01)
*A61K 38/01* (2006.01)
*A61K 9/16* (2006.01)

(52) U.S. Cl.
CPC ............ *A61K 38/38* (2013.01); *A61K 9/1658* (2013.01); *A61K 9/1688* (2013.01); *A61K 36/8994* (2013.01); *A61K 38/012* (2013.01); *A61K 2236/37* (2013.01); *A61K 2236/53* (2013.01)

(58) Field of Classification Search
None
See application file for complete search history.

(56) References Cited

U.S. PATENT DOCUMENTS

| | | | | |
|---|---|---|---|---|
| 5,444,089 A | * | 8/1995 | Li | A61K 31/23 514/547 |
| 2013/0171276 A1 | * | 7/2013 | Kim | A61K 36/605 424/728 |
| 2018/0009842 A1 | * | 1/2018 | Chen | C07K 1/36 |

FOREIGN PATENT DOCUMENTS

| CN | 101724675 | * | 6/2010 |
|---|---|---|---|
| CN | 102094057 | * | 6/2011 |

* cited by examiner

*Primary Examiner* — Ralph J Gitomer
(74) *Attorney, Agent, or Firm* — Raymond Y. Chan

(57) ABSTRACT

The present invention discloses a preparation method of an albumin peptide combination and the action of inhibiting the proliferation of cancer cells thereof, the preparation steps comprise: mixing albumin and water in proportion, heating, adjusting pH, adding alkaline protease to perform enzymatic hydrolysis, deactivating, filtrating; mixing *Coix* seed and water in proportion, decocting to extract, filtrating, adding certain proportional of water to filter residue, continue decocting to extract, collecting filtrates, determining solid matter content respectively, mixing two solutions, concentrating, spray drying, and obtaining an albumin peptide combination having the action of inhibiting the proliferation of cancer cells. The present invention found that, as compared with using *Coix* seed individually, the effect of inhibiting the proliferation of cancer cells of albumin peptide combination is stronger, and process is simpler.

6 Claims, 1 Drawing Sheet

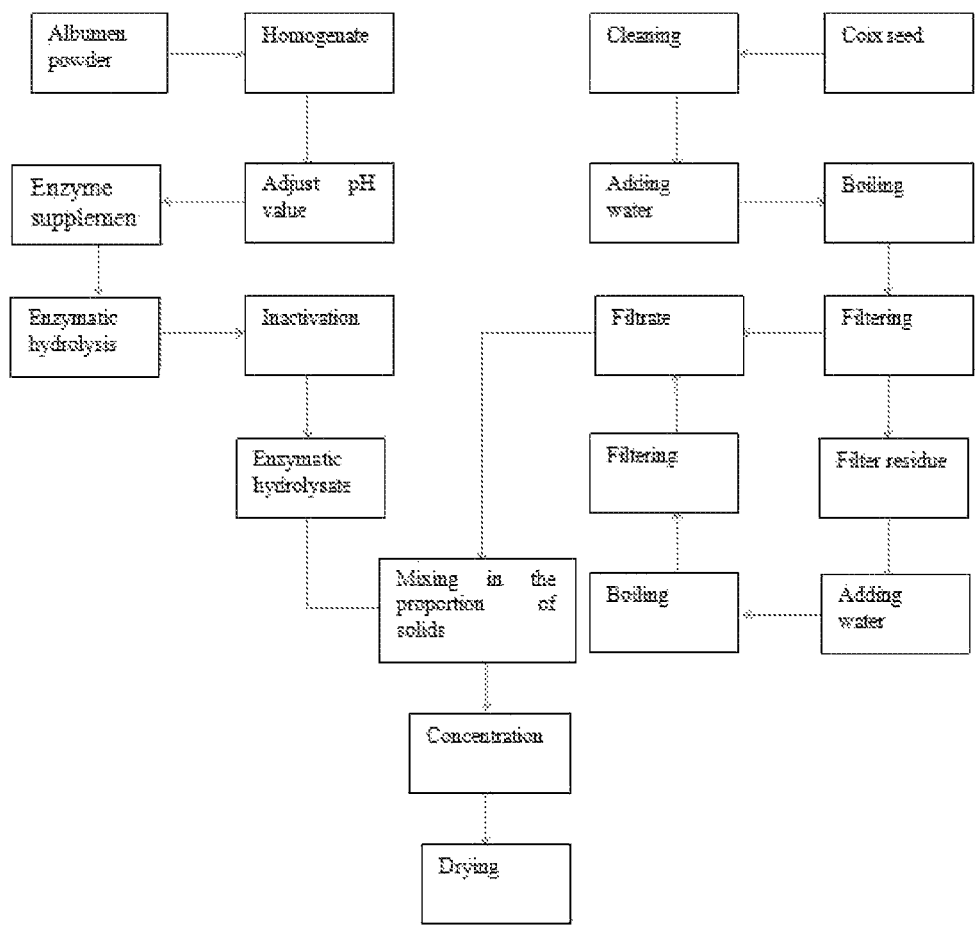

PREPARATION METHOD OF ALBUMIN PEPTIDE COMBINATION HAVING THE ACTION OF INHIBITING THE PROLIFERATION OF CANCER CELLS

CROSS REFERENCE OF RELATED APPLICATION

This is a non-provisional application that claims the benefit of priority under 35 U.S.C. § 119 to Chinese application number 21610527097.0, filed Jul. 6, 2016, wherein the entire contents of each of which is expressly incorporated herein by reference.

NOTICE OF COPYRIGHT

A portion of the disclosure of this patent document contains material which is subject to copyright protection. The copyright owner has no objection to any reproduction by anyone of the patent disclosure, as it appears in the United States Patent and Trademark Office patent files or records, but otherwise reserves all copyright rights whatsoever.

BACKGROUND OF THE PRESENT INVENTION

Field of Invention

The present invention relates to a preparation method of the albumin peptide combination having the action of inhibiting the proliferation of cancer cells.

Description of Related Arts

The latest version "World Cancer Report" indicates that pathogenesis condition is most severe in developing countries of Africa, Asia, Central and South America, and the like. 14 million cancer cases were newly added worldwide in 2012 and 8.2 million people died, wherein 3.07 million cancer cases were newly added in China and 3.2 million people died, taking 21.9% and 26.8% of worldwide total amount respectively. The National Cancer Registry issued in 2012 indicates that about 3.5 million cancer cases were newly added in China annually and about 2.5 million people died consequently.

Cancer is also known as malignant tumor. Tumor refers to the topical lump formed by cell abnormal proliferation of topical tissue. Benign tumor is cleaned up easily, generally free from metastasis, free from recurrence, and only has compression and obstruction action to organ and tissue. However, malignant tumor can destroy the structure and function of tissue and organ, causing necrosis, hemorrhage and co-infection. Patients may eventually die due to organ function failure.

Albumin polypeptide is a small molecular oligopeptide taking egg white as raw material, and is prepared via manufacturing processes of enzymatic hydrolysis, isolating, refining, drying and the like, with molecular weight of 200-800 Dalton, wherein the nutrient ingredients contained in egg are abundant and comprehensive, and thus it is referred to as "human ideal nutrient pool". Nutritionists call it "complete protein mode". Egg white proteins contain plentiful of proteins and a plurality of amino acids essential to human body. The composition and match of amino acids are good in proportionality and are a kind of protein with utilization rate of organism higher. Albumin peptide is a small molecular polypeptide taking egg white as raw material, extracted by utilizing modern bioengineering technology via enzyme digestion, having character of easy absorption and high in bioavailability etc., and meanwhile having a plurality of physiological function and irreplaceable advantage in terms of both nutrient and healthcare.

Proteins and polypeptides are closely associated with the body immunity. Literatures report that protein malnutrition may cause extensive atrophy of lymphoid tissue, especially the thymus, spleen, lymph node and the like of children will be affected, causing the morphology of tissue subjected to change. Experiments indicate that albumin peptide has the synergic action for the immunologic function. Therefore, supplementing albumin peptide can promote the recovery of the function of immunologic tissue and enhance the disease resistant ability of the organism. It is very beneficial for juvenile, children and elders to resist the invasion of viruses and bacteria and enhance disease resistant capability. As a small molecular protein peptide due to having smaller molecular weight, albumin peptide can keep the nutritive value of albumin, directly absorbed by human body without digestion, and quickly supply the nutrients required by human body. Albumin peptide contains 20 essential and non-essential amino acids required by human body, wherein the composition and match of amino acids are good in proportionality and can be used as single raw material to develop the product of this type. Albumin peptide has action of regulating immunity and can be extensively used in the field of health-care food and medical food.

*Coix* seed (also known as jobstears seed) has very high nutrition value and is honored as "King of gramineous plants worldwide". *Coix* seed, slight sweet and rich in nutrient, comprises carbohydrates in mass ratio 52% to 80%, proteins in mass ratio 13% to 17%, and fats in mass ratio 4% to 7%. *Coix* seed oils are mainly unsaturated fatty acid, wherein linoleic acid is in mass ratio of 34% and has special coixenolide. *Coix* seed can also be milled for pasta, which is a health-care food with very high nutrient value. Being used as herbal medicine, *Coix* seed has effects of strengthening spleen, diuresis, clearing heat, and relieving cough. The present invention is a series of research work carried out on the basis of Chinese traditional herbal.

SUMMARY OF THE PRESENT INVENTION

The technical problem to be solved by the present invention is to overcome the defects of the prior art and provide a preparation method of the albumin peptide combination having the action of inhibiting the proliferation of cancer cells. The mixture has dramatic effect of inhibiting the proliferation of cancer cells and the preparation method is simple.

In order to solve the above technical problem, the present invention provides the following technical schemes:

An albumin peptide combination having the action of inhibiting the proliferation of cancer cells, comprising raw materials comprise an albumin enzymatic hydrolysate and a *Coix* seed extract under mass ratio of 5:2 to 5, wherein a content of a solid matter of the albumin enzymatic hydrolysate is 15% to 35% and a content of a solid matter of the *Coix* seed extract is 10% to 30%.

Preferably, a preparation method of the albumin enzymatic hydrolysate is as follows:

(1) adding an albumin into water that is 5 to 20 times to the mass thereof, heating the albumin and water mixture to 40° C. to 50° C., and homogenizing for producing a solution;

(2) adjusting pH of the solution after the homogenizing of step (1) to 7 to 9, adding an alkaline protease at 3% to 5% of the mass of the solution to perform enzymatic hydrolysis reaction for 5 h to 10 h for producing an enzymatic hydrolysate;

(3) heating the enzymatic hydrolysate of step (2) to boil, deactivating for 0.5 h to 2 h; and (4) cooling the enzymatic hydrolysate after the deactivating of step (3) to 60° C. to 80° C., performing filtration to obtain the albumin enzymatic hydrolysate.

In any one of the above schemes, preferably, the filtration process in step (4) is plate frame filtration.

In any one of the above schemes, preferably, the preparation method of the Coix seed extract is as follows:

(1) decocting first Coix seeds with boiling water for 3 h to 5 h, wherein the amount of water is 10 to 15 times of the mass of the first Coix seeds, subsequently, performing filtration;

(2) decocting second Coix seeds with boiling water for 1 h to 3 h, wherein the amount of water is 5 to 10 times of the mass of the second Coix seeds, subsequently, performing filtration; and (3) combining filtrates of the two filtrations from step (1) and step (2) to obtain the Coix seed extract.

In any one of the above schemes, preferably, the filtration process in steps (1) and (2) is plate frame filtration.

The present application further provides a preparation method of the albumin peptide combination having the action of inhibiting the proliferation of cancer cells, comprising each step as follows:

(1) adding an albumin into water that is 5 to 20 times to the mass thereof, heating the albumin and water mixture to 40° C. to 50° C., and homogenizing for producing a solution;

(2) adjusting pH of the solution after the homogenizing of step (1) to 7 to 9, adding an alkaline protease at 3% to 5% of the mass of the solution to perform enzymatic hydrolysis reaction for 5 h to 10 h for producing an enzymatic hydrolysate;

(3) heating the enzymatic hydrolysate of step (2) to boil, deactivating for 0.5 h to 2 h;

(4) cooling the enzymatic hydrolysate after the deactivating of step (3) to 60° C. to 80° C., performing filtration to obtain the albumin enzymatic hydrolysate.

(5) decocting first Coix seeds with boiling water for 3 h to 5 h, wherein the amount of water is 10-15 times of the mass of the first Coix seeds, subsequently, performing filtration;

(6) decocting second Coix seeds with boiling water for 1 h to 3 h, wherein the amount of water is 5 to 10 times of the mass of the second Coix seeds, subsequently, performing filtration;

(7) combining the filtrates of the two filtrations from step (5) and step (6) to obtain the Coix seed extract;

(8) performing solid matter determination for the filtrate of the albumin peptide enzymatic hydrolysate and the Coix seed extract respectively, mixing the albumin peptide enzymatic hydrolysate and the Coix seed extract under appropriate ratio; and (9) performing low temperature vacuum concentration to the mixed liquid of step (8), wherein temperature is 40° C. to 60° C. and pressure is 0.03 MPA to 0.07 MPa, subsequently, spray drying, wherein the temperature of the wind at inlet is 180° C. to 220° C. and the temperature of the wind at outlet is 80° C. to 110° C., preparing the albumin peptide combination having the action of inhibiting the proliferation of cancer cells.

Preferably, all the filtration processes are plate frame filtration.

The albumin peptide combination having the action of inhibiting the proliferation of cancer cells of the present invention can be applied to foods, functional foods and pharmaceuticals.

The beneficial effects of the present invention: in the product of the albumin peptide combination prepared in the present invention, the content of polypeptide is greater than 20% and the content of total carbohydrate is greater than 10%. Compared with the prior art, the present invention first combined the albumin peptide and Coix seed extract as product, wherein the content of albumin peptide is 3.75% and the content of Coix seed extract is 3%, by using the albumin enzymatic hydrolysate obtained by hydrolysis of alkaline protease and Coix seed water extract by the method of solid matter determination, after mixing, concentrating through low temperature vacuum in proportion, spray drying, and obtaining the mixture of albumin peptide and Coix seed extract. The mixture of albumin peptide and Coix seed extract is used to inhibit the proliferation of cancer cells. The albumin peptide combination having the action of inhibiting the proliferation of cancer cells is prepared and obtained through the above method. The mixture of the present invention has dramatic effect of inhibiting cancer cells. The present invention simplifies the preparation process of traditional process, wherein condensation and drying are combined and completed in one step, saves the process of mixing after drying materials, greatly saves labor cost and enhances product quality.

BRIEF DESCRIPTION OF THE DRAWINGS

FIG. 1 is a process flow chart of the preparation method of the albumin peptide combination having the action of inhibiting the proliferation of cancer cells of the present invention.

DETAILED DESCRIPTION OF THE PREFERRED EMBODIMENT

The following description is disclosed to enable any person skilled in the art to make and use the present invention. Preferred embodiments are provided in the following description only as examples and modifications will be apparent to those skilled in the art. The general principles defined in the following description would be applied to other embodiments, alternatives, modifications, equivalents, and applications without departing from the spirit and scope of the present invention.

The followings are the illustration performed to the preferable examples of the present application, it shall be understood that, the preferable examples described herein are merely used to illustrate and explain the present invention, but not used to define the present invention.

Example 1 an Albumin Peptide Combination Having the Action of Inhibiting the Proliferation of Cancer Cells The preparation method comprises each step as follows:

(1) adding an albumin into water that is 20 times to the mass thereof, heating the albumin and water mixture to 50° C., and homogenizing for producing a solution;

(2) adjusting the acidity of the solution after the homogenizing of step (1) to pH 8 by dilute sodium hydroxide, adding an alkaline protease at 3% of the mass of the solution, performing enzymatic hydrolysis for 8 h for producing hydrolysate;

(3) heating the hydrolysate after the enzymatic hydrolysis to boil, deactivating for 0.5 h;

(4) cooling the hydrolysate after the deactivating of step (3) to 60° C., performing plate frame filtration.

(5) decocting first *Coix* seeds with boiling water for 3 h, wherein the amount of water is 10 times of the mass of the first *Coix* seeds, performing plate frame filtration;

(6) decocting second *Coix* seeds with boiling water for 1 h, wherein the amount of water is 5 times of the mass of the second *Coix* seeds, performing plate frame filtration;

(7) combining the filtrates of the two filtrations from step (5) and step (6);

(8) performing solid matter determination for the filtrate of the albumin peptide enzymatic hydrolysate and the *Coix* seed extract respectively, wherein the content of the solid matter of the albumin enzymatic hydrolysate is 17.3% and the content of the solid matter of the *Coix* seed extract is 22.8%, mixing the two under ratio of 5:3 by total weight;

(9) performing low temperature vacuum concentration to the mixed liquid, wherein temperature is 60° C. and pressure is 0.07 MPa, spray drying to prepare final product, wherein the temperature of the wind at inlet is 200° C. and the temperature of the wind at outlet is 90° C.

In the final product, the content of polypeptide is greater than 38.7%, the content of total carbohydrate is greater than 21.1%, and moisture 4.1%, which meets the requirement in the product standard that the content of polypeptide is greater than 20% and the content of total carbohydrate is greater than 10%.

Example 2 a Preparation of the Albumin Peptide Combination Having the Action of Inhibiting the Proliferation of Cancer Cells The preparation method comprises each step as follows:

(1) adding an albumin into water that is 10 times to the mass thereof, heating the albumin and water mixture to 50° C., homogenizing for producing a solution;

(2) adjusting the acidity of the solution after the homogenizing of step (1) to pH 9 by dilute sodium hydroxide, adding an alkaline protease at 4% of the mass of the solution, performing enzymatic hydrolysis for 6 h for producing hydrolysate;

(3) heating the hydrolysate after the enzymatic hydrolysis to boil, deactivating for 0.5 h;

(4) cooling the hydrolysate after the deactivating of step (3) to 60° C., performing plate frame filtration.

(5) decocting first *Coix* seeds with boiling water for 5 h, wherein the amount of water is 15 times of the mass of the first *Coix* seeds, performing plate frame filtration;

(6) decocting second *Coix* seeds with boiling water for 3 h, wherein the amount of water is 10 times of the mass of the second *Coix* seeds, performing plate frame filtration;

(7) combining the filtrates of the two filtrations from step (5) and step (6);

(8) performing solid matter determination for the filtrate of the albumin peptide enzymatic hydrolysate and the *Coix* seed extract respectively, wherein the content of the solid matter of the albumin enzymatic hydrolysate is 31.3% and the content of the solid matter of the *Coix* seed extract is 21.9%, mixing the two under ratio of 5:4 by total weight;

(9) performing low temperature vacuum concentration to the mixed liquid, wherein temperature is 60° C. and pressure is 0.03 MPa, spray drying to prepare final product, wherein the temperature of the wind at inlet is 200° C. and the temperature of the wind at outlet is 90° C.

In the final product, the content of polypeptide is greater than 39.0%, the content of total carbohydrate is greater than 20.3%, and moisture 4.5%, which meets the requirement in the product standard that the content of polypeptide is greater than 20% and the content of total carbohydrate is greater than 10%.

Example 3 a Preparation of the Albumin Peptide Combination Having the Action of Inhibiting the Proliferation of Cancer Cells The preparation method comprises each step as follows:

(1) adding an albumin into water that is 10 times to the mass thereof, heating the albumin and water mixture to 50° C., homogenizing for producing a solution;

(2) adjusting the acidity of the solution after the homogenizing of step (1) to pH 9 by dilute sodium hydroxide, adding an alkaline protease at 3% of the mass of the solution, performing enzymatic hydrolysis for 7 h for producing hydrolysate;

(3) heating the hydrolysate after the enzymatic hydrolysis to boil, deactivating for 0.5 h;

(4) cooling the hydrolysate after the deactivating of step (3) to 60° C., performing plate frame filtration.

(5) decocting first *Coix* seeds with boiling water for 4 h, wherein the amount of water is 13 times of the mass of the first *Coix* seeds, performing plate frame filtration;

(6) decocting second *Coix* seeds with boiling water for 2 h, wherein the amount of water is 8 times of the mass of the second *Coix* seeds, performing plate frame filtration;

(7) combining the filtrates of the two filtrations from step (5) and step (6);

(8) performing solid matter determination for the filtrate of the albumin peptide enzymatic hydrolysate and the *Coix* seed extract respectively, wherein the content of the solid matter of the albumin enzymatic hydrolysate is 30.9% and the content of the solid matter of the *Coix* seed extract is 21.3%, mixing the two under ratio of 5:4 by total weight;

(9) performing low temperature vacuum concentration to the mixed liquid, wherein temperature is 60° C. and pressure is 0.03 MPa; spray drying to prepare final product, wherein the temperature of the wind at inlet is 205° C. and the temperature of the wind at outlet is 93° C.

In the final product, the content of polypeptide is greater than 38.8%, the content of total carbohydrate is greater than 20.2%, and moisture 4.3%, which meets the requirement in the product standard that the content of polypeptide is greater than 20% and the content of total carbohydrate is greater than 10%.

Example 4 a Preparation of the Albumin Peptide Combination Having the Action of Inhibiting the Proliferation of Cancer Cells The preparation method comprises each step as follows:

(1) adding an albumin into water that is 5 times to the mass thereof, heating the albumin and water mixture to 40° C., homogenizing for producing a solution;

(2) adjusting the acidity of the solution after the homogenizing of step (1) to pH 7 by dilute sodium hydroxide, adding an alkaline protease at 5% of the mass of the solution, performing enzymatic hydrolysis for 10 h for producing hydrolysate;

(3) heating the hydrolysate after the enzymatic hydrolysis to boil, deactivating for 2 h;

(4) cooling the hydrolysate after the deactivating of step (3) to 60° C., performing plate frame filtration.

(5) decocting first *Coix* seeds with boiling water for 4 h, wherein the amount of water is 13 times of the mass of the first *Coix* seeds, performing plate frame filtration;

(6) decocting second *Coix* seeds with boiling water for 2 h, wherein the amount of water is 8 times of the mass of the second *Coix* seeds, performing plate frame filtration;

(7) combining the filtrates of the two filtrations from step (5) and step (6);

(8) performing solid matter determination for the filtrate of the albumin peptide enzymatic hydrolysate and the *Coix* seed extract respectively, wherein the content of the solid matter of the albumin enzymatic hydrolysate is 15% and the content of the solid matter of the *Coix* seed extract is 10%, mixing the two under ratio of 5:2 by total weight;

(9) performing low temperature vacuum concentration to the mixed liquid, wherein temperature is 40° C. and pressure is 0.03 MPa, spray drying to prepare final product, wherein the temperature of the wind at inlet is 180° C., the temperature of the wind at outlet is 110° C.

In the final product, the content of polypeptide is greater than 38.0%, the content of total carbohydrate is greater than 20.0%, and moisture 4.1%, which meets the requirement in the product standard that the content of polypeptide is greater than 20% and the content of total carbohydrate is greater than 10%.

Example 5 the Inhibition Experiment of Different Albumin Peptide Combination Solutions to Hepatoma Cells Preparing and obtaining tested sample group solutions with concentrations of low dose group 10 mg/L, medium dose group 30 mg/L and high dose group 50 mg/L respectively, according to the albumin peptide combination obtained by the process of Example 3.

Preparing the *Coix* seed extract solution with concentration of 13.3 mg/L as control group, according to the preparation method of the process of the *Coix* seed extract in Example 3.

Taking Cell Culture Solution as Blank Group.

Taking the human hepatoma cell SMMC-7721 in logarithmic growth phase, pouring out culture solution, adding 0.25% pancreatin solution, after digesting under 37° C. for 2-3 min, observing cells under inverted microscope, pouring out digesting solution when 80% cells become round. Adding culture solution 4 mL having the addition amount of 20% calf serum, pipetting repeatedly, to make all cells washed down, pipetting slightly to mix homogeneously, preparing single cell suspension, adjusting culture solution to make the concentration of cell to be 105/mL, taking 105/mL cell suspension, inoculating 96 wells plate at 195 μL per well, after culturing for 24 h, adding 5 μL for each of tested sample solutions of different doses as well as blank group and control group solution, setting 6 parallel wells for each. After culturing for 2 days, adding 5 mg/mL MTT 20 μL per well, continue culturing for 4 h, sucking out culture solution, adding 150 μL DMSO, vibrating slightly to dissolve crystallization, determining absorbance value by automatic microplate reader at 490 nm, calculating the inhibition ratio of cell group according to following formula.

Inhibition rate of cell growth (Ig)=(1−the absorbance of administration group/the absorbance of black group)×100%

Experimental Results:

Referring to table 1, the comparison between the inhibitory effect of the low dose group, medium dose group and high dose group of tested samples to the growth of human hepatoma cell SMMC-7721 and blank group has dramatic difference. Tested sample group has action of inhibiting the growth of human hepatoma cell SMMC-7721, wherein its inhibitory action is superior to that of control group. The inhibitory action to the growth of human hepatoma cell SMMC-7721 of albumin peptide combination is superior to that of *Coix* seed extract individually.

TABLE 1

Comparison experiment between albumin peptide combination and coix seed to the effect of inhibiting the growth of human hepatoma cell SMMC-7721

| | Blank group | Control group | Sample low dose group | Sample medium dose group | Sample high dose group |
|---|---|---|---|---|---|
| Inhibition rate(%) | 0.37 | 23.2 | 41.5 | 54.3 | 52.6 |

Example 6 the Inhibition Experiment of Albumin Peptide Combination Solutions of Different Concentrations to Gastric Carcinoma Cell Preparing and obtaining tested sample group solutions with concentrations of low dose group 10 mg/L, medium dose group 30 mg/L and high dose group 50 mg/L respectively, according to the albumin peptide combination obtained by the process of Example 3.

Preparing the *Coix* seed extract solution with concentration of 13.3 mg/L as control group, according to the preparation method of the process of the *Coix* seed extract in Example 3.

Taking Cell Culture Solution as Blank Group.

Taking the human gastric carcinoma cell BGC823 in logarithmic growth phase, using culture solution to dilute to prepare cell suspension, adjusting the concentration of cell to be 5×104/mL. Taking 96 wells culture plate, setting blank group, control group and tested sample group, inoculating cell suspension into 96 wells culture plate according to designing scheme, adding cell suspension 200 μL into each well. Culturing 96 wells culture plate in 5% CO2 incubator under 37° C. for 24 h, pouring out supernatant, adding 20 μL albumin peptide combination solutions of different concentrations respectively for tested sample group, then adding culture solution to 200 μL, adding 20 μL *Coix* seed extract solution for control group, then adding culture solution to 200 μL, directly adding culture solution for blank group to sufficient amount, mixing homogenously; setting 6 parallel wells for each group, continue culturing for 24 h, pouring out supernatant, adding 5 mg/mL MTT 20 μL per well, culture solution 180 μL. Centrifuging 96 wells culture plate under condition of 1000 r/min for 10 min, sucking and discarding the supernatant in wells carefully, adding DMSO 100 μL per well, vibrating slightly to dissolve crystallization, determining absorbance value by automatic microplate reader at 490 nm, calculating the inhibition ratio of cell group according to following formula.

Inhibition rate of cell growth (Ig)=(1−the absorbance of administration group/the absorbance of blank group)×100%

Experimental Results:

Referring to table 2, the comparison between the inhibitory effect of the low dose group, medium dose group and high dose group of tested samples to the growth of human gastric carcinoma cell BGC823 and blank group has dramatic difference. Tested sample group has action of inhibiting the growth of human gastric carcinoma cell BGC823, wherein its inhibitory action is superior to that of control group. The inhibitory action to the growth of human gastric carcinoma cell BGC823 of albumin peptide combination is superior to that of *Coix* seed extract individually.

TABLE 2

Comparison experiment between albumin peptide combination and coix seed to the effect of inhibiting the growth of human gastric carcinoma cell BGC823

|  | Blank group | Control group | Sample low dose group | Sample medium dose group | Sample high dose group |
|---|---|---|---|---|---|
| Inhibition rate(%) | 0.41 | 19.2 | 46.5 | 59.1 | 61.7 |

Example 7 the Inhibition Experiment of Albumin Peptide Combination Solutions of Different Concentrations to Human Lung Carcinoma Cell SPC-A1

Preparing and obtaining tested sample group solutions with concentrations of low dose group 10 mg/L, medium dose group 30 mg/L and high dose group 50 mg/L respectively, according to the albumin peptide combination obtained by the process of Example 3.

Preparing the *Coix* seed extract solution with concentration of 13.3 mg/L as control group, according to the preparation method of the process of the *Coix* seed extract in Example 3.

Taking Cell Culture Solution as Blank Group.

Taking the human lung carcinoma cell SPC-A1 in logarithmic growth phase, using culture solution to dilute to prepare cell suspension, adjusting the concentration of cell to be 5×104/mL. Taking 96 wells culture plate, setting blank group, control group and tested sample group, inoculating cell suspension into 96 wells culture plate according to designing scheme, adding cell suspension 200 μL into each well. Culturing 96 wells culture plate in 5% CO2 incubator under 37° C. for 24 h, pouring out supernatant, adding 20 μL albumin peptide combination solutions of different concentrations respectively for tested sample group, then adding culture solution to 200 μL, adding 20 μL *Coix* seed extract solution for control group, then adding culture solution to 200 μL, directly adding culture solution for blank group to sufficient amount, mixing homogenously; setting 6 parallel wells for each group, continue culturing for 24 h, pouring out supernatant, adding 5 mg/mL MTT 20 μL per well, culture solution 180 μL. Centrifuging 96 wells culture plate under condition of 1000 r/min for 10 min, sucking and discarding the supernatant in wells carefully, adding DMSO 100 μL per well, vibrating slightly to dissolve crystallization, determining absorbance value by automatic microplate reader at 490 nm, calculating the inhibition rate of cell group according to following formula.

Inhibition rate of cell growth (Ig)=(1−the absorbance of administration group/the absorbance of blank group)×100%

Experimental Results:

Referring to table 3, the comparison between the inhibitory effect of the low dose group, medium dose group and high dose group of tested samples to the growth of human lung carcinoma cell SPC-A1 and blank group has dramatic difference. Tested sample group has dramatic action of inhibiting the growth of human lung carcinoma cell SPC-A1, wherein its inhibitory action is superior to that of control group. The inhibitory action to the growth of human lung carcinoma cell SPC-A1 of albumin peptide combination is superior to that of *Coix* seed extract individually.

TABLE 3

Comparison experiment between albumin peptide combination and coix seed to the effect of inhibiting the growth of human lung carcinoma cell SPC-A1

|  | Blank group | Control group | Sample low dose group | Sample medium dose group | Sample high dose group |
|---|---|---|---|---|---|
| Inhibition rate(%) | 0.29 | 18.1 | 38.9 | 51.2 | 59.3 |

Example 8 the Inhibition Experiment of Albumin Peptide Combination Solutions of Different Concentrations to Human Cervical Cancer Cell Hela Preparing and obtaining tested sample group solutions with concentrations of low dose group 10 mg/L, medium dose group 30 mg/L and high dose group 50 mg/L respectively, according to the albumin peptide combination obtained by the process of Example 3.

Preparing the *Coix* seed extract solution with concentration being 13.3 mg/L as control group, according to the preparation method of the process of the *Coix* seed extract in Example 3.

Taking Cell Culture as Blank Group.

Taking the human cervical cancer cell Hela in logarithmic growth phase, using culture solution to dilute to prepare cell suspension, adjusting the concentration of cell to be 5×104/mL. Taking 96 wells culture plate, setting blank group, control group and tested sample groups, inoculating cell suspension into 96 wells culture plate according to designing scheme, adding cell suspension 200 μL into each well. Culturing 96 wells culture plate in 5% CO2 incubator under 37° C. for 24 h, pouring out supernatant, adding 20 μL albumin peptide combination solutions of different concentrations respectively for tested sample group, then adding culture solution to 200 μL, adding 20 μL *Coix* seed extract solution for control group, then adding culture solution to 200 μL, directly adding culture solution for blank group to sufficient amount, mixing homogenously; setting 6 parallel wells for each group, continue culturing for 72 h, pouring out supernatant, adding 5 mg/mL MTT 20 μL per well, continue culturing for 4 h. Centrifuging 96 wells culture plate under condition of 1000 r/min for 10 min, sucking and discarding the supernatant in wells carefully, adding DMSO 100 μL per well, vibrating slightly to dissolve crystallization, determining absorbance value by automatic microplate reader at 490 nm, calculating the inhibition ratio of cell group according to following formula.

Inhibition rate of cell growth (Ig)=(1−the absorbance of administration group/the absorbance of blank group)×100%

Experimental Results:

Referring to table 4, the comparison between the inhibitory effect of the low dose group, medium dose group and high dose group of tested samples to the growth of human cervical cancer cell Hela and blank group has dramatic difference. Tested sample group has action of inhibiting the growth of human cervical cancer cell Hela, wherein its inhibitory action is superior to that of control group. The inhibitory action to the growth of human cervical cancer cell Hela of albumin peptide combination is superior to that of *Coix* seed extract individually.

TABLE 4

Comparison experiment between albumin peptide combination and coix seed to the effect of inhibiting the growth of human cervical cancer cell Hela

|  | Blank group | Control group | Sample low dose group | Sample medium dose group | Sample high dose group |
|---|---|---|---|---|---|
| Inhibition rate(%) | 0.49 | 23.8 | 45.8 | 56.7 | 63.2 |

It shall be stated last that: the above is merely preferably Examples of the present invention, but not used to define the present invention. Though detailed explanation is performed to the present invention with reference to aforethe Examples, as to a person skilled in the art, he still can perform amendment to the technical schemes recorded in aforethe each Example, or perform equivalent substitution to a part of technical features therein. Any amendments, equivalent substitution, improvement and the like made within the spirit and principle of the present invention shall be included in the protection scope of the present invention.

One skilled in the art will understand that the embodiment of the present invention as shown in the drawings and described above is exemplary only and not intended to be limiting.

It will thus be seen that the objects of the present invention have been fully and effectively accomplished. The embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. A preparation method of an albumin peptide combination having the action of inhibiting the proliferation of cancer cells, wherein the albumin peptide combination, having an action of inhibiting a proliferation of cancer cells, comprising: raw materials including an albumin enzymatic hydrolysate and a *Coix* seed extract under mass ratio of 5:2 to 5, wherein a content of a solid matter of the albumin enzymatic hydrolysate is 15% to 35% and a content of a solid matter of the *Coix* seed extract is 10% to 30%, wherein the preparation method comprises the steps of:

(1) adding albumin into water that is 5 to 20 times to a mass thereof, heating the albumin and water mixture to 40° C. to 50° C., and homogenizing for producing a solution;

(2) adjusting pH of the solution after the homogenizing of step (1) to 7 to 9, adding an alkaline protease at 3% to 5% of the mass of the solution to perform enzymatic hydrolysis reaction for 5 h to 10 h for producing a hydrolysis solution;

(3) heating the hydrolysis solution of the step (2) to boil, and inactivating the hydrolysis solution for 0.5 h to 2 h;

(4) cooling the hydrolysis solution after the inactivating step (3) to 60° C. to 80° C., and performing filtration to obtain the albumin enzymatic hydrolysate;

(5) decocting first *Coix* seeds with boiling water for 3 h to 5 h, wherein an amount of water is 10 to 15 times of a mass of the first *Coix* seeds, subsequently, performing filtration;

(6) decocting second *Coix* seeds with boiling water for 1 h to 3 h, wherein an amount of water is 5 to 10 times of a mass of the second *Coix* seed, subsequently, performing filtration;

(7) combining filtrates of the two filtrations of the step (5) and the step (6) to obtain the *Coix* seed extract;

(8) mixing the albumin peptide enzymatic hydrolysate and the *Coix* seed extract; and (9) performing low temperature vacuum concentration to the mixture of the albumin peptide enzymatic hydrolysate and the *Coix* seed extract in the step (8) to prepare the albumin peptide combination having the action of inhibiting the proliferation of cancer cells, wherein temperature is 40° C. to 60° C. and pressure is 0.03 MPa to 0.07 MPa, subsequently, spray drying, wherein the temperature of air at an inlet is 180° C. to 220° C. and the temperature of the air at an outlet is 80° C. to 110° C.

2. The preparation method, as recited in claim 1, wherein the step (4) is a filtration process that is a plate frame filtration.

3. The preparation method, as recited in claim 1, wherein all the filtration processes are plate frame filtration.

4. The preparation method, as recited in claim 1, wherein the albumin peptide combination is in form of one of powders, granules, tablets, capsules, and oral solution.

5. The preparation method, as recited in claim 2, wherein the albumin peptide combination is in form of one of powders, granules, tablets, capsules, and oral solution.

6. The preparation method, as recited in claim 3, wherein the albumin peptide combination is in form of one of powders, granules, tablets, capsules, and oral solution.

* * * * *